(12) United States Patent
Pulley et al.

(10) Patent No.: US 11,471,444 B2
(45) Date of Patent: Oct. 18, 2022

(54) METHODS OF INHIBITING TUMOR METASTASIS

(71) Applicant: Vanderbilt University, Nashville, TN (US)

(72) Inventors: Jill M. Pulley, Nashville, TN (US); Robert R. Lavieri, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 16/767,534

(22) PCT Filed: Nov. 29, 2018

(86) PCT No.: PCT/US2018/062967
§ 371 (c)(1),
(2) Date: May 27, 2020

(87) PCT Pub. No.: WO2019/108736
PCT Pub. Date: Jun. 6, 2019

(65) Prior Publication Data
US 2020/0405694 A1    Dec. 31, 2020

Related U.S. Application Data

(60) Provisional application No. 62/592,365, filed on Nov. 29, 2017.

(51) Int. Cl.
| *A61K 31/422* | (2006.01) |
| *A61P 35/04*  | (2006.01) |
| *A61K 45/06*  | (2006.01) |

(52) U.S. Cl.
CPC ............ *A61K 31/422* (2013.01); *A61P 35/04* (2018.01); *A61K 45/06* (2013.01)

(58) Field of Classification Search
CPC ........ A61K 31/422; A61K 45/06; A61P 35/04
See application file for complete search history.

(56) References Cited

U.S. PATENT DOCUMENTS

| 4,839,384 A | 6/1989 | Ogletree |
| 5,066,480 A | 11/1991 | Ogletree et al. |
| 5,100,889 A | 3/1992 | Misra et al. |
| 5,153,327 A | 10/1992 | Misra et al. |
| 5,158,967 A | 10/1992 | Hall |
| 5,260,449 A | 11/1993 | Singh et al. |
| 5,312,818 A | 5/1994 | Rubin et al. |
| 5,332,840 A | 7/1994 | Real et al. |
| 5,399,725 A | 3/1995 | Poss et al. |
| 5,508,445 A | 4/1996 | Poss et al. |
| 5,512,690 A | 4/1996 | Poss et al. |
| 5,539,130 A | 7/1996 | Poss et al. |
| 5,605,917 A | 2/1997 | Ogletree |
| 5,618,946 A | 4/1997 | Poss et al. |
| 8,551,489 B2 | 10/2013 | Moussa et al. |
| 9,173,889 B2 | 11/2015 | Oliva |
| 9,283,266 B2 | 3/2016 | Suckow et al. |
| 2003/0109544 A1 | 6/2003 | Harrigan et al. |
| 2009/0311224 A1 | 12/2009 | Lee et al. |
| 2010/0166707 A1 | 7/2010 | Hunter et al. |
| 2011/0086030 A1 | 4/2011 | Ware |
| 2017/0226514 A1 | 8/2017 | Offermanns et al. |

FOREIGN PATENT DOCUMENTS

WO    WO2009089098 A1    7/2009

OTHER PUBLICATIONS

Patent Office of the Cooperation Council for the Arab States of the Gulf Examination Report for Application No. 2018-36551 dated Jan. 7, 2021 (5 pages).
Patent Office of the Cooperation Council for the Arab States of the Gulf Examination Report for Application No. 2018-36551 dated Nov. 14, 2021 (4 pages).
European Patent Office Extended Search Report for Application No. 18884156.3 dated Oct. 8, 2021 (9 pages).
Li et al., "Inhibiting breast cancer by targeting the thromboxane A2 pathway", Nature Partner Journals Precision Oncology, vol. 1, No. 1, 2017, 8 pages.
Mayer, "Ifetroban in Treating Patients with Malignant Solid Tumors at High Risk of Metastatic Recurrence", 2018, pp. 1-9.
Nie et al., "Thromboxane A2 Regulation of Endothelial Cell Migration, Angiogenesis, and Tumor Metastasis", Biochemical and Biophysical Research Communications, vol. 267, 2000, pp. 245-251.
Honn et al., "Inhibition of tumor cell metastasis by modulation of the vascular prostacyclin/thromboxane A2 system", Clin Expl. Metastasis, vol. 1, No. 2, 1983, pp. 103-114.
Zhang et al., "Abstract 3445: Targeting Thromboxane A2 Receptor (TP) to block breast cancer metastasis", Tumor Biology, vol. 72, No. 8 Supplement, 2012, 3 pages.
Andree et al., "Challenges in circulating tumor cell detection by the CellSearch system", Mol Oncol, 2016, vol. 10, No. 3, pp. 395-407.
Balic et al., "Micrometastasis: detection methods and clinical importance", Cancer Biomark Sect Dis Markers, vol. 9(1-6), 2011, pp. 397-419.
Best et al., "RNA-Seq of Tumor-Educated Platelets Enables Blood-Based Pan-Cancer, Multiclass, and Molecular Pathway Cancer Diagnostics", Cancer Cell, 2015, vol. 28, No. 5, pp. 666-676.
Coyle et al., "Add-Aspirin: A phase III, double-blind, placebo controlled, randomised trial assessing the effects of aspirin on disease recurrence and survival after primary therapy in common non-metastatic solid tumours", Contemp Clin Trials, 2016, vol. 51, pp. 56-64.
Culp et al., "Earliest Steps in Primary Tumor Formation and Micrometastasis Resolved with Histochemical Markers of Gene-tagged Tumor Cells", J Histochem Cytochem. 1998, vol. 46, No. 5, pp. 557-567.

(Continued)

*Primary Examiner* — Kamal A Saeed
(74) *Attorney, Agent, or Firm* — Michael Best & Friedrich LLP

(57) ABSTRACT

Thromboxane A2 receptor antagonists, such as ifetroban, inhibit solid tumor metastasis. The formation of surface and microscopic lung metastases are inhibited. Thromboxane A2 receptor antagonists can inhibit the tumor metastasis process without affecting the growth or development of a primary tumor.

14 Claims, 8 Drawing Sheets

(56) References Cited

OTHER PUBLICATIONS

Denny et al., "PheWAS: demonstrating the feasibility of a phenome-wide scan to discover gene-disease associations.", Bioinformatics, 2010, vol. 26, No. 9, pp. 1205-1210.
Ekambaram et al., "The thromboxane synthase and receptor signaling pathway in cancer: an emerging paradigm in cancer progression and metastasis", Cancer Metastasis Rev, Dec. 2011, vol. 30, No. 3-4, pp. 397-408.
Fabisiewicz et al., "CTC clusters in cancer progression and metastasis", Med Oncol, 2017, vol. 34, No. 12, p. 1-12.
Gay et al., "Contribution of platelets to tumor metastasis", Nat Rev Cancer, 2011, vol. 11, No. 2, pp. 123-134.
Gu et al., "Elevated Platelet to Lymphocyte Ratio Is Associated with Poor Survival Outcomes in Patients with Colorectal Cancer", PloS One., 2016, 11(9):e0163523, 14 pages.
Gu et al., "Pre-treatment Elevated Platelet Count Associates with HER2 Overexpression and Prognosis in Patients with Breast Cancer", Asian Pac J Cancer Prev, 2015, vol. 16, No. 13, pp. 5537-5540.
Guillem-Llobat et al., "Aspirin prevents colorectal cancer metastasis in mice by splitting the crosstalk between platelets and tumor cells", Oncotarget., May 2016, vol. 7, No. 22, pp. 32462-32477.
Honn et al., "Inhibition by dihydropyridine class calcium channel blockers of tumor cell-platelet-endothelial cell interactions in vitro and metastasis in vivo", Biochem Pharmacology, 1985, No. 34, vol. 2, pp. 235-241.
Honn et al., "Inhibition of tumor cell-platelet interactions and tumor metastasis by the calcium channel blocker, nimodipine", Clin Exp Metastasis, 1984, vol. 2, No. 1, pp. 61-72.
Hoshino et al., "Tumour exosome integrins determine organotropic metastasis", Nature, 2015, vol. 527, No. 7578, pp. 329-335.
Ji et al., "Elevated platelet count is a strong predictor of poor prognosis in stage I non-small cell lung cancer patients", Platelets, 2015, vol. 26, No. 2, pp. 138-142.
Jiang et al., "Microfluidic isolation of platelet-covered circulating tumor cells", Lab Chip., 2017, vol. 17, No. 20, pp. 3498-3503.
Jin et al., "Molecular insights into tumour metastasis: tracing the dominant events", J Pathol., 2017, vol. 241, No. 5, pp. 567-577.
Juratli et al., "In Vivo Long-Term Monitoring of Circulating Tumor Cells Fluctuation during Medical Interventions", Aboussekhra A, editor. PLOS One, 2015 vol. 10, No. 9, p. e0137613, 12 pages.
Koh et al., "Utility of pre-treatment neutrophil-lymphocyte ratio and platelet-lymphocyte ratio as prognostic factors in breast cancer", Br J Cancer, 2015, vol. 113, No. 1, pp. 150-158.
Langsenlehner et al., "Evaluation of the platelet-to-lymphocyte ratio as a prognostic indicator in a European cohort of patients with prostate cancer treated with radiotherapy", Urol Oncol.: Seminars and Original Investigations, 2015, vol. 33, No. 5, pp. 201.e9-16.
Leblanc et al., "Metastasis: new functional implications of platelets and megakaryocytes", Blood, 2016, vol. 128, No. 1, pp. 24-31.
Li et al., "Genetic engineering of platelets to neutralize circulating tumor cells", Journal of Controlled Release, 2016, 228, pp. 38-47.
Li et al., "Platelet-to-lymphocyte ratio acts as a prognostic factor for patients with advanced hepatocellular carcinoma", Tumour Biol., 2 015, vol. 36, No. 4, pp. 2263-2269.
Lord et al., "Significance of extranodal tumour deposits in colorectal cancer: A systematic review and meta-analysis", European Journal of Cancer, 2017, vol. 82, pp. 92-102.
Man et al., "Pretreatment plasma D-dimer, fibrinogen, and platelet levels significantly impact prognosis in patients with epithelial ovarian cancer independently of venous thromboembolism", Int J Gynecol Cancer, 2015 vol. 25, No. 1, pp. 24-32.
Manegold, "Platelet-endothelial interaction in tumor angiogenesis and microcirculation", Blood, 2003, vol. 101, No. 5, pp. 1970-1976.
Massagué et al., "Metastatic colonization by circulating tumour cells", Nature, 2016, vol. 529, pp. 298-306.
Matsui et al., "Thromboxane A2 receptor signaling facilitates tumor colonization through P-selectin-mediated interaction of tumor cells with platelets and endothelial cells", Cancer Sci., 2012, vol. 103, No. 4, pp. 700-707.

Miao et al., "Neutrophil to lymphocyte ratio and platelet to lymphocyte ratio are predictive of chemotherapeutic response and prognosis in epithelial ovarian cancer patients treated with platinum-based chemotherapy", Cancer Biomarkers, 2016, vol. 17, No. 1, pp. 33-40.
Michael et al., "Platelet microparticles infiltrating solid tumors transfer miRNAs that suppress tumor growth", Blood, 2017, vol. 130, No. 5, pp. 567-580.
Ogawa et al., "Effect of a novel thromboxane A2 synthetase inhibitor on ischemia-induced mitochondrial dysfunction in canine hearts", Arzneimittelforschung, 1988, vol. 38, No. 2, pp. 228-230.
Onoda et al., "Antithrombogenic effects of calcium channel blockers: synergism with prostacyclin and thromboxane synthase inhibitors", Thromb Res., 1984, vol. 34, No. 5, pp. 367-378.
Pang et al., "Significance of platelet count and platelet-based models for hepatocellular carcinoma recurrence", World Journal of Gastroenterol, 2015, vol. 21, No. 18, pp. 5607-5621.
Patrignani et al., "Aspirin and Cancer", Journal of the American College of Cardiology, 2016, vol. 68, No. 9, pp. 967-976.
Peinado et al., "Pre-metastatic niches: organ-specific homes for metastases", Nature Review, 2017, vol. 17, No. 5, pp. 302-317.
Powe et al., "Beta-Blocker Drug Therapy Reduces Secondary Cancer Formation in Breast Cancer and Improves Cancer Specific Survival", Oncotarget, 2010, vol. 1, No. 7, pp. 628-638.
Pulley et al., "Accelerating Precision Drug Development and Drug Repurposing by Leveraging Human Genetics", ASSAY Drug Dev Technologies, 2017, vol. 15, No. 3, pp. 113-119.
Quail et al., "Microenvironmental regulation of tumor progression and metastasis", Nature Medicine, 2013, vol. 19, No. 11, pp. 1423-1437.
Roop et al., "A Randomized Phase II Trial Investigating the Effect of Platelet Function Inhibition on Circulating Tumor Cells in Patients With Metastatic Breast Cancer", Clin Breast Cancer, 2013, vol. 13, No. 6, pp. 409-415.
Saloman et al., "Can Stopping Nerves, Stop Cancer?" Trends in Neuroscience, 2016, vol. 39, No. 12, pp. 880-889.
Serebruany et al., "Solid cancers after antiplatelet therapy: Confirmations, controversies, and challenges", Thromb Haemost., 2015, vol. 114, No. 6, pp. 1104-1112.
Suo et al., "Proportion of circulating tumor cell clusters increases during cancer metastasis", Cytometry Part A., 2017, vol. 91, No. 3, pp. 250-253.
Talmadge et al., "AACR Centennial Series: The Biology of Cancer Metastasis: Historical Perspective", Cancer Research, 2010, vol. 70, No. 14, pp. 5649-5669.
Timar et al., "Calcium channel blocker treatment of tumor cells induces alterations in the cytoskeleton, mobility of the integrin alpha IIb beta 3 and tumor-cell-induced platelet aggregation", J Cancer Res Clin Oncol., 1992, vol. 118, No. 6, pp. 425-434.
Tohme et al., "Surgery for Cancer: A Trigger for Metastases", Cancer Res., 2017 vol. 77, No. 7, pp. 1548-1552.
Vivian et al., "Mitochondrial Genomic Backgrounds Affect Nuclear DNA Methylation and Gene Expression", Cancer Res., 2017, pp. 6202-6214.
Wang et al., "Electron cryotomography reveals ultrastructure alterations in platelets from patients with ovarian cancer", Proc Natl Acad Sci, 2015, vol. 112, No. 46, pp. 14266-14271.
Wang et al., "The pretreatment platelet and plasma fibrinogen level correlate with tumor progression and metastasis in patients with pancreatic cancer", Platelets, 2014, vol. 25, No. 5, pp. 382-387.
Wells et al., "Targeting tumor cell motility as a strategy against invasion and metastasis", Trends Pharmacol Sci., 2013, No. 34, vol. 5, pp. 283-289.
Wojtukiewicz et al., "Antiplatelet agents for cancer treatment: a real perspective or just an echo from the past?", Cancer Metastasis Rev., 2017, pp. 305-329.
Wojtukiewicz et al., "Thrombin—unique coagulation system protein with multifaceted impacts on cancer and metastasis", Cancer Metastasis Rev., 2016, vol. 35, No. 2, pp. 213-233.
Xia et al., "Predictive value of pre-transplant platelet to lymphocyte ratio for hepatocellular carcinoma recurrence after liver transplantation", World J Surg Oncol., 2015, vol. 13, No. 1, 7 pages.

(56) References Cited

OTHER PUBLICATIONS

Zhang et al., "Prognostic value of platelet to lymphocyte ratio in non-small cell lung cancer: a systematic review and meta-analysis", Sci Rep., 2016, vol. 6, 6 pages.
International Search Report and Written Opinion for Application No. PCT/US18/62967 dated Feb. 5, 2019 (7 pages).
Taiwanese Office Action for application 107142806, dated Aug. 10. 2022, 10 pages with translation.

METHODS OF INHIBITING TUMOR METASTASIS

RELATED APPLICATIONS

This patent application is the U.S. national stage entry, under 35 U.S.C. § 371, of International Application Number PCT/US2018/062967, filed Nov. 29, 2018, which claims priority to U.S. Provisional Application No. 62/592,365, filed Nov. 29, 2017, the entire contents of each of which are incorporated herein by reference.

TECHNICAL FIELD

The invention provides methods of inhibiting solid tumor metastasis with thromboxane A2 receptor antagonists.

BACKGROUND

Cancer remains a leading cause of morbidity and mortality globally. For the majority of cancers, cytotoxic chemotherapy has been the standard of care for decades, although emerging advances in targeted therapies and immunotherapeutic strategies are altering the reliance on chemotherapy for some cancers. Despite advances in how some cancers are treated, cancer metastasis and recurrence are universal concerns across all solid cancers diagnosed in early stage.

Metastatic cancer diagnoses impose a significant emotional, social, and economic burden that impacts quality of life for each patient, in large part because these diagnoses generally associate with early death. Even when a cancer is in remission (a clinically silent state), microscopic metastases, even single cancer cells, can lurk clinically undetectable throughout the body for variably long periods of time, depending on the type of cancer. These potentially dangerous cells remain unseen, even to the most sensitive imaging modalities, until they grow to a level that becomes clinically apparent.

Few therapies directly target tumor cell invasion and/or metastasis and none are currently in FDA-approved clinical use for this indication. Deliberate approaches to specifically prevent metastases by neutralizing or thwarting the problematic dispersion of tumor cells would be important, and could manifest in a number of different forms: containment of cells to the primary site, disabling cancer cell survival in the circulation, reducing evasion of immune surveillance, preventing platelet/tumor cell aggregates, preventing extravasation at secondary sites, and/or making secondary sites inhospitable to metastatic seeding. Agents that specifically affect the metastatic process across cancers would thus represent a new paradigm in cancer management, addressing an unmet medical need and aimed ultimately at blocking dissemination of cancers—focusing beyond the primary tumor.

Blockade of metastasis may have additional indirect benefits as well. For example, agents that thwart the spread of cancer might allow conventional chemotherapies to be used at reduced doses or for shorter durations. This is an important consideration, since chemotherapies often target fast-growing healthy cells in addition to fast growing tumor cells, causing treatment-associated toxicity, tissue damage, and morbidity. Further, treatments aimed at preventing metastatic dissemination might be used in combination with molecularly targeted anti-tumor agents. In this scenario, it should be noted that acquired resistance to molecularly targeted agents often arises at sites of metastatic recurrence. Thus, inhibition of metastatic dissemination may reduce the incidence and/or rate of acquired resistance, improving the clinical success of precision cancer therapeutics.

Patients diagnosed with solid cancers might receive any one or a combination of treatments, including surgery, radiation, chemotherapy, vaccines, hormone modulators, immunotherapies, or molecularly targeted therapies. After the treatment course, including the treatment of any micrometastatic disease with adjuvant systemic therapy, a patient may have no remaining clinical evidence of cancer. In these cases, the cancer is considered to be 'in remission'. These patients, their families, and their physicians rely on watchful waiting until the time clinical evidence of cancer returns. Prevention of initial or secondary metastatic spread of any remaining tumor cells—by targeting the metastatic process itself—could replace watchful waiting with proactive prevention.

There is a need therefore for effective therapies that block or inhibit the spread or metastasis of solid tumors from a primary tumor site.

SUMMARY

In one aspect, the invention provides a method of inhibiting solid tumor metastasis comprising administering to a subject in need thereof, an amount of a thromboxane A2 receptor antagonist effective to inhibit metastasis of a solid tumor in the subject.

In another aspect, the invention provides a thromboxane A2 receptor antagonist, or a pharmaceutically acceptable salt or composition thereof, for use in the treatment or inhibition of solid tumor metastasis in a subject.

In another aspect, the invention provides a thromboxane A2 receptor antagonist, or a pharmaceutically acceptable salt or composition thereof, for use in a method of treating or inhibiting solid tumor metastasis, wherein the method comprises administering the thromboxane A2 receptor antagonist to a subject in need thereof.

In another aspect, the invention provides a use of a thromboxane A2 receptor antagonist, or a pharmaceutically acceptable salt or composition thereof, for the preparation of a medicament for the treatment or inhibition of solid tumor metastasis in a subject.

DETAILED DESCRIPTION

Cancer Metastasis

Cancers can spread at different rates and employ distinct molecular and cellular pathways in one patient as compared to others. Some of this variability may be attributable to a host environment that is more or less conducive to metastatic spread. In contrast to local tissue invasion by cancer cells, metastasis requires the transport of cancer cells to distant sites via the blood and/or lymphatic system; perineural invasion can also play an important role in a number of cancers. Cancer metastasis may involve the detachment and embolization of tumor cell aggregates, which may be increased in size via interaction with hematopoietic cells within the circulation. Other aspects of metastasis include the circulation of tumor emboli within the vasculature (both hematologic and lymphatic), the survival of tumor cells that trafficked through the circulation and arrest in a capillary bed, and the extravasation of the tumor embolus, by mechanisms similar to those involved in the initial tissue invasion.

"Metastasis of a tumor/cancer cell", as used herein, refers to the dissemination/transmission of a tumor/cancer cell from an original site to one or more noncontiguous sites elsewhere in the body, e.g., from one organ or part to another not directly connected with it by way of, for example, blood vessels or lymphatics. The metastasis of a tumor/cancer cell can, for example, lead to the formation of a secondary or subsequent tumor at a site other than the location of the primary tumor. The tumor/cancer cell of the inventive methods can be a cell of any solid tumor/cancer, such as those described herein.

Distinct from the metastasis process (i.e., dissemination/transmission) is the growth of a metastatic tumor/cancer at a secondary site, which can involve proliferation of the tumor cells within the organ parenchyma resulting in a metastatic focus, establishment of vascularization, and defenses against host immune responses.

Selected platelet-mediated steps in metastasis that it may be possible to target via pharmacological agents include: detachment and embolization of platelet-containing tumor cell aggregates; circulating tumor cells protected from host immune responses by aggregated platelets; and tumor embolus colonization facilitated by P-selectin-mediated tumor cell-platelet interactions.

Figure 6:
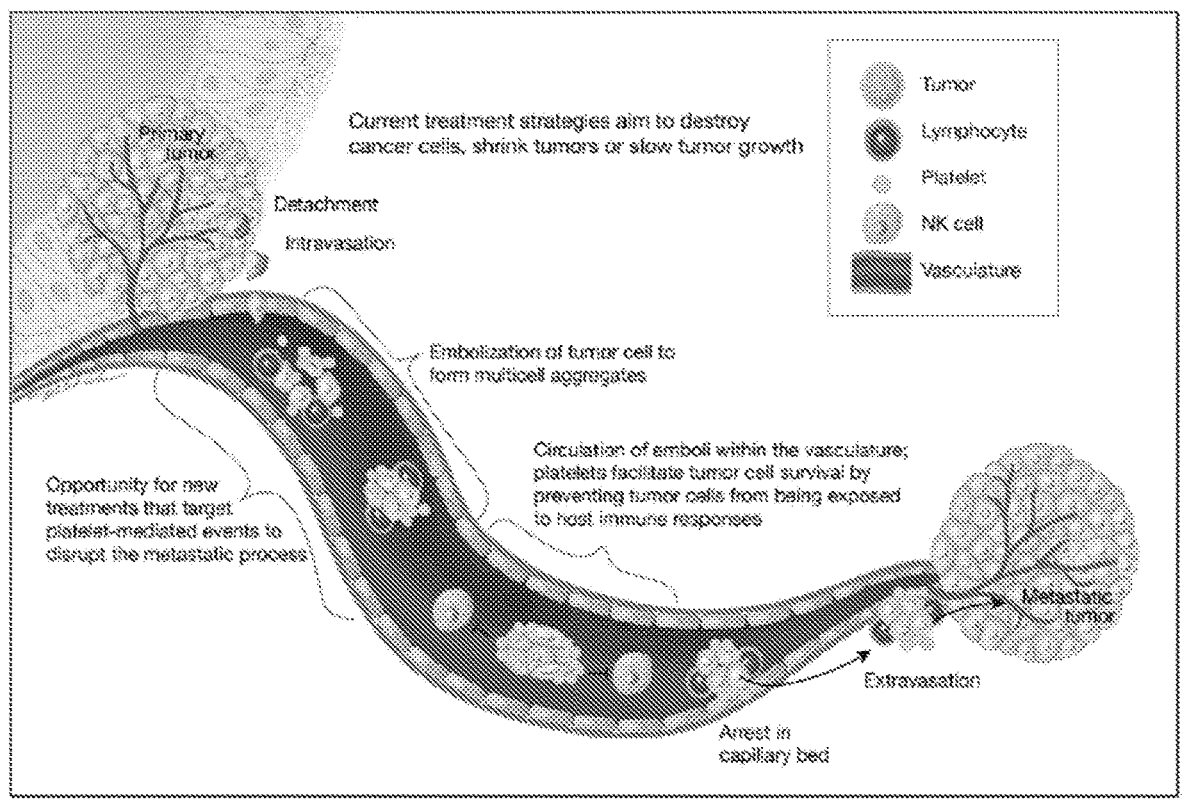
FIG. 6 shows a conceptual rendering of a proposed solid tumor metastasis process.

While a number of investigations indicate involvement of platelets in the path to cancer metastasis (see FIG. 6), research exploring the manipulation of these connections to inhibit platelet activation with the deliberate goal of preventing or interrupting metastatic disease remains at a very early stage. No such proven therapies yet exist. The diverse ways in which platelets interact with tumor cells and the complex directionality of those effects are yet incompletely understood and FIG. 6 is not intended to be an exhaustive representation of this field; for example, much remains unexplored regarding interactions between platelets and tumor cells, the role that other factors may play in the overall disease process, and the potential benefit of antiplatelet therapeutics, including factors such as intercellular transfer of mitochondrial DNA and various observed epigenetic changes.

Thromboxane A2 receptor antagonists may have broad utility in solid tumor metastasis inhibition or prevention, across multiple tumor/cancer types. Without being bound by a particular theory, thromboxane A2 receptor antagonists decrease platelet aggregation and may decrease the ability of tumor cells to detach from the vascular endothelium and attach to platelets. Through blockade of platelet aggregation with tumor cells, thromboxane A2 receptor antagonists may decrease circulating tumor cell survival through decreased integrin- and/or selectin-mediated cell survival signaling. Thromboxane A2 receptor antagonists may prevent colonization by affecting P-selectin-mediated interactions. Platelets may shield circulating tumor cell clusters from host immune responses. Through blockade of platelet aggregation with tumor cells, thromboxane A2 receptor antagonists may disrupt the interactions between platelets and tumor cell clusters, thereby increasing exposure of circulating tumor cells to host immune responses and inhibiting metastasis. Thromboxane A2 receptor antagonists may inhibit the formation of circulating tumor cell clusters, the movement of circulating tumor cell clusters, and/or the aggregation of circulating tumor cell clusters with platelets.

Methods of Inhibiting Tumor Metastasis

One aspect of the invention encompasses a method for inhibiting tumor cell metastasis in a subject. The method comprises administering an amount of a thromboxane A2 receptor antagonist effective to inhibit metastasis of a solid tumor in the subject.

The invention also provides a thromboxane A2 receptor antagonist, or a pharmaceutically acceptable salt or composition thereof, for use in the treatment or inhibition of solid tumor metastasis in a subject. The invention also provides a thromboxane A2 receptor antagonist, or a pharmaceutically acceptable salt or composition thereof, for use in a method of treating or inhibiting solid tumor metastasis, wherein the method comprises administering the thromboxane A2 receptor antagonist to a subject in need thereof. The treatment or inhibition of solid tumor metastasis comprises use of the thromboxane A2 receptor antagonist in an amount effective to inhibit metastasis of a solid tumor in a subject.

The invention also provides the use of a thromboxane A2 receptor antagonist, or a pharmaceutically acceptable salt or composition thereof, for the preparation of a medicament in the treatment or inhibition of solid tumor metastasis in a subject. The invention also provides the use of a thromboxane A2 receptor antagonist, or a pharmaceutically acceptable salt or composition thereof, for the preparation of a medicament in a method of treating or inhibiting solid tumor metastasis, wherein the method comprises administering the thromboxane A2 receptor antagonist to a subject in need thereof. The treatment or inhibition of solid tumor metastasis comprises use of the thromboxane A2 receptor antagonist in an amount effective to inhibit metastasis of a solid tumor in a subject.

Inhibition of tumor cell metastasis may be manifested by a reduction in the overall metastatic burden, e.g., the number, distribution, or volume of metastatic tumors in the treated subject relative to an untreated subject. In one embodiment, the number of metastatic tumors may be reduced at least two-fold. In another embodiment, the number of metastatic tumors may be reduced at least ten-fold. In still another embodiment, the number of metastatic tumors may be reduced at least 50-fold. In yet another embodiment, the number of metastatic tumors may be reduced at least 200-fold. In a further embodiment, the number of metastatic tumors may be reduced to such an extent such that no metastatic tumors are detectable. In still another embodiment, metastatic tumors may be restricted to one organ or tissue, rather than being spread to two or more organs or tissues.

Inhibition of metastasis may be measured by many parameters in accordance with the present invention and, for instance, may be assessed by delayed appearance of secondary tumors, slowed development of secondary tumors, decreased occurrence of secondary tumors, slowed or decreased severity of secondary effects of disease, arrested tumor growth, reduced rate of metastatic recurrence, and regression of tumors, among others. In the extreme, complete inhibition is referred to herein as prevention. In addition, the inhibition of metastasis may be identified by a reduction in metastatic foci present in the animal. In still another embodiment, inhibition of metastasis may manifest as a period of metastasis free survival in a treated subject. In some embodiments, a thromboxane A2 receptor antagonist is administered in an amount effective to effective to reduce the rate of metastatic recurrence.

In some embodiments, a thromboxane A2 receptor antagonist is administered in an amount effective to inhibit metastasis of a solid tumor in a subject without inhibiting the growth/development of the solid tumor itself, i.e., at a primary/secondary site. Thus, the thromboxane A2 receptor antagonist may inhibit the metastatic process without affecting the growth or development of a primary/secondary tumor.

The subject may be a mammal, such as a human patient. Non-human animals include companion animals, such as cats, dogs and horses. Other types of non-human animals envisioned for treatment according to the present methods include commercially important animals, including sheep, swine, cattle and others.

The primary cancer may be a cancer of epithelial origin. The primary cancer type may be lung cancer, non-small cell lung cancer, breast cancer, ovarian cancer, prostate cancer, testicular cancer, pancreatic cancer, melanoma, sarcoma, cervical cancer, endometrial cancer, liver cancer, uterine cancer, kidney (renal)cancer, gastroesophageal cancer, colon cancer, bladder cancer, mouth cancer, or throat cancer.

The types of metastasis that may be inhibited and/or eliminated include metastasis to the lung and/or bone (such as to the spine). It is envisioned that the present methods and preparations will also find utility in reducing and/or preventing the metastasis of tumor/cancer cells to other organs, such as, by way of example and not limitation, metastasis to ovary, liver, brain, kidney, spleen, intestines, adrenal glands, or any other tissue and/or organ or combination of tissues and/or organs.

Thromboxane A2 receptor antagonists suitable for use in the disclosed methods include, but are not limited to ifetroban, GR32191, SQ29548, sulotroban, daltroban, linotroban, ramatroban, seratrodast, terutroban, Z-235, LCB-2853, SQ28668, ICI 192605, AH23848, ONO3708, CPI-211, or pinane $TXA_2$. Suitable thromboxane A2 receptor antagonists are also described in U.S. Pat. No. 5,100,889, which is incorporated herein by reference.

For example, the thromboxane A2 receptor antagonist may have formula (I)

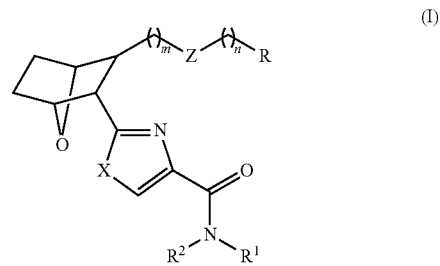

including all stereoisomers thereof, wherein
m is 1, 2, or 3;
n is 0, 1, 2, 3, or 4;
Z is —$(CH_2)_2$—, —CH=CH—, or

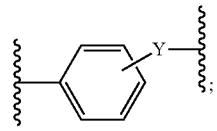

Y is O, a single bond, or —CH=CH—;
R is $CO_2H$, $CO_2C_{1-6}$alkyl, $CH_2OH$, —$CONHSO_2R^3$, —$CONHR^{3a}$, or —$CH_2$-tetrazol-5-yl;
$R^3$ is $C_{1-6}$alkyl, 6- to 10-membered aryl, or -L-(6- to 10-membered aryl);
$R^{3a}$ is $C_{1-6}$alkyl, 6- to 10-membered aryl, or -$L^1$-(6- to 10-membered aryl);
X is O, S, or NH;
$R^1$ is hydrogen, $C_{1-8}$alkyl, $C_{2-8}$alkenyl, $C_{2-8}$alkynyl, $G^1$, -$L^1$-$G^1$, —$(CH_2)_t$—C(O)—$NHR^{1a}$, or —$(CH_2)_t$—NH—$C(O)R^{1a}$;
$G^1$ is a 6- to 10-membered aryl, a $C_{3-12}$cycloalkyl, a 5- to 12-membered heteroaryl, or a 4- to 12-membered heterocyclyl;
$L^1$ is $C_{1-6}$alkylene;
t is 1 to 12;
$R^{1a}$ is $C_{1-6}$alkyl, $C_{3-12}$cycloalkyl, -$L^1$-$C_{3-12}$cycloalkyl, or a 6- to 10-membered aryl;
$R^2$ is hydrogen, $C_{1-6}$alkyl, 6- to 10-membered aryl, or -$L^1$-(6- to 10-membered aryl);
or $R^1$ and $R^2$ together with the nitrogen to which they attach form a 4- to 8-membered heterocyclic ring;
wherein each aryl is independently and optionally substituted with 1 or 2 substituents independently selected from the group consisting of halogen, cyano, $C_{1-6}$alkyl, $C_{1-6}$haloalkyl, OH, —$OC_{1-6}$alkyl, —$OC_{1-6}$haloalkyl, —$SC_{1-6}$alkyl, —$S(O)C_{1-6}$alkyl, —$S(O)_2C_{1-6}$alkyl, —$OC_{1-6}$alkylene-phenyl, —S-phenyl, —S(O)-phenyl, and —$S(O)_2$-phenyl;
wherein each cycloalkyl is independently and optionally substituted with 1-4 substituents independently selected from the group consisting of halogen, $C_{1-6}$alkyl, $C_{1-6}$haloalkyl, OH, and —$OC_{1-6}$alkyl.

Thromboxane A2 receptor antagonists include compounds of formula (I-a), (I-b), (I-c), (I-d), (I-e), and (I-f), wherein Z is —$(CH_2)_2$— or —CH=CH—.

(I-a) 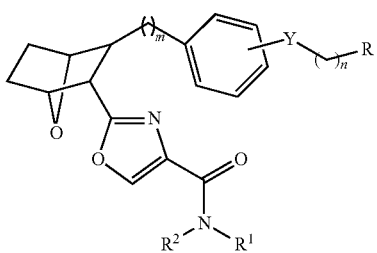

(I-b) 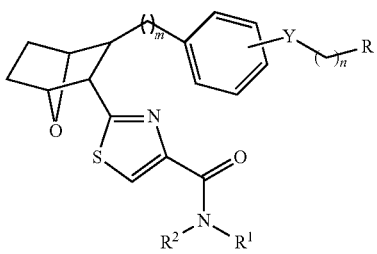

(I-c) 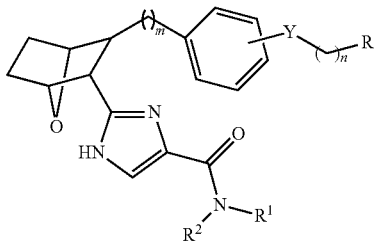

(I-d) 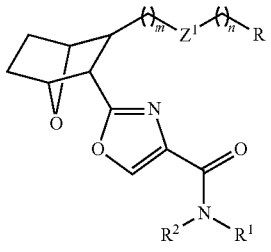

(I-e) 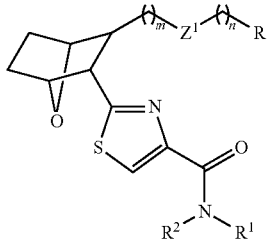

(I-f) 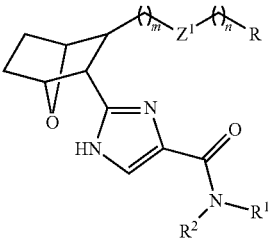

In some embodiments $Z^1$ is —CH=CH—. In further embodiments, $Z^1$ is —CH=CH—, m is 1 and n is 2. In still further embodiments, $Z^1$ is —CH=CH— and R is $CO_2H$.

In formula (I), Z may be

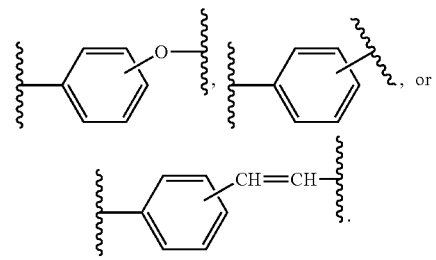

In some embodiments, formula (I) has formula (I-g), wherein R, $R^1$, $R^2$, X, m, and n are as defined herein.

(I-g) 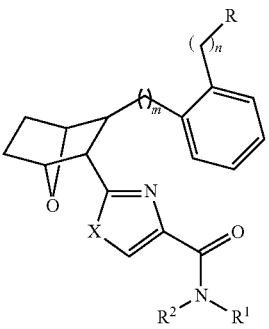

In some embodiments, formula (I) has formula (I-h), wherein R, $R^1$, $R^2$, X, m, and n are as defined herein.

(I-h) 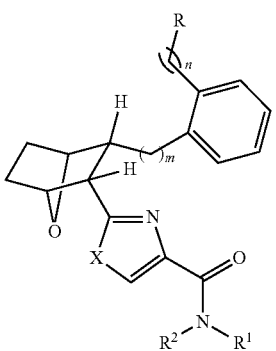

Included in the formulas (I) and (I-a) to (I-h) are compounds wherein m is 1, n is 2, R is $CO_2H$, $R^2$ is hydrogen, and $R^1$ is $C_{1-8}$alkyl. According to any compounds of formulas (I), (I-g), or (I-h) are compounds wherein X is O.

The thromboxane A2 receptor antagonist may be in the form of a pharmaceutically acceptable salt. For example, in formulas (I) and (I-a) to (I-h), the group $CO_2H$ at R may be in the form of an alkali metal salt, such as the sodium salt (i.e., $R=CO_2Na$).

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry," 5th edition (1989), Longman Scientific & Technical, Essex CM20 2JE, England, or (2) direct separation of the mixture of optical enantiomers on chiral chromatographic columns, or (3) fractional recrystallization methods.

The present disclosure also includes an isotopically-labeled compound, which is identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^{2}H$, $^{3}H$, $^{13}C$, $^{14}C$, $^{15}N$, $^{18}O$, $^{17}O$ $^{31}P$, $^{32}P$, $^{35}S$, $^{18}F$, and $^{36}Cl$, respectively. Substitution with heavier isotopes such as deuterium, i.e. $^{2}H$, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

The term "alkyl," as used herein, means a straight or branched, saturated hydrocarbon chain. The term "lower alkyl" or "$C_{1-6}$alkyl" means a straight or branched chain hydrocarbon containing from 1 to 6 carbon atoms. The term "$C_{1-4}$alkyl" means a straight or branched chain hydrocarbon containing from 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl," as used herein, means a straight or branched, hydrocarbon chain containing at least one carbon-carbon double bond.

The term "alkylene," as used herein, refers to a divalent group derived from a straight or branched chain hydrocarbon, for example, of 1 to 6 carbon atoms. Representative examples of alkylene include, but are not limited to, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—.

The term "aryl," as used herein, refers to a phenyl or a phenyl appended to the parent molecular moiety and fused to a cycloalkyl group (e.g., indanyl), a phenyl group (i.e., naphthyl), or a non-aromatic heterocycle (e.g., benzo[d][1,3]dioxol-5-yl).

The term "cycloalkyl," as used herein, refers to a saturated ring system containing all carbon atoms as ring members and zero double bonds. A cycloalkyl may be a monocyclic cycloalkyl (e.g., cyclopropyl), a fused bicyclic cycloalkyl (e.g., decahydronaphthalenyl), or a bridged cycloalkyl in which two non-adjacent atoms of a ring are linked by an alkylene bridge of 1, 2, 3, or 4 carbon atoms (e.g., bicyclo[2.2.1]heptanyl). Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, and bicyclo[1.1.1]pentanyl.

The term "halogen" or "halo," as used herein, means Cl, Br, I, or F.

The term "haloalkyl," as used herein, means an alkyl group, as defined herein, in which one, two, three, four, five, six, seven or eight hydrogen atoms are replaced by a halogen.

The term "heteroaryl," as used herein, refers to an aromatic monocyclic heteroatom-containing ring (monocyclic heteroaryl) or a bicyclic ring system containing at least one monocyclic heteroaryl (bicyclic heteroaryl). The monocyclic heteroaryl are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl is an 8- to 12-membered ring system having a monocyclic heteroaryl ring fused to a monocyclic aromatic or carbocyclic ring, a monocyclic heteroaryl, or a monocyclic heterocycle. The bicyclic heteroaryl is attached to the parent molecular moiety at an aromatic ring atom. Representative examples of heteroaryl include, but are not limited to, indolyl (e.g., indol-1-yl, indol-2-yl, indol-4-yl), pyridinyl (including pyridin-2-yl, pyridin-3-yl, pyridin-4-yl), pyrimidinyl, pyrazinyl, pyridazinyl, pyrazolyl (e.g., pyrazol-4-yl), pyrrolyl, benzopyrazolyl, 1,2,3-triazolyl (e.g., triazol-4-yl), 1,3,4-thiadiazolyl, 1,2,4-thiadiazolyl, 1,3,4-oxadiazolyl, 1,2,4-oxadiazolyl, imidazolyl, thiazolyl (e.g., thiazol-4-yl), isothiazolyl, thienyl, benzimidazolyl (e.g., benzimidazol-5-yl), benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl (e.g., indazol-4-yl, indazol-5-yl), quinazolinyl, 1,2,4-triazinyl, 1,3,5-triazinyl, isoquinolinyl, quinolinyl, 6,7-dihydro-1,3-benzothiazolyl, imidazo[1,2-a]pyridinyl (e.g., imidazo[1,2-a]pyridin-6-yl), naphthyridinyl, pyridoimidazolyl, thiazolo[5,4-b]pyridin-2-yl, thiazolo[5,4-d]pyrimidin-2-yl.

The term "heterocycle" or "heterocyclic," as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, 2-oxo-3-piperidinyl, 2-oxoazepan-3-yl, oxadiazolinyl, oxadiazolidinyl, oxazolinyl, oxazolidinyl, oxetanyl, oxepanyl, oxocanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, a monocyclic heterocycle fused to a monocyclic heteroaryl, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. The bicyclic heterocycle is attached to the parent molecular moiety at a non-aromatic ring atom (e.g., 2-oxaspiro[3.3]heptan-6-yl, indolin-1-yl, hexahydrocyclopenta[b]pyrrol-1(2H)-yl). Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, 2-oxa-6-azaspiro[3.3]heptan-6-yl, azabicyclo[2.2.1]heptyl (including 2-azabicyclo[2.2.1]hept-2-yl), azabicyclo[3.1.0]hexanyl (including 3-azabicyclo[3.1.0]hexan-3-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.13,7]decane), and oxa-adamantane (2-oxatricyclo[3.3.1.13,7]decane). The monocyclic, bicyclic, and tricyclic heterocycles are connected to the parent molecular moiety at a non-aromatic ring atom.

Terms such as "alkyl," "cycloalkyl," "alkylene," etc. may be preceded by a designation indicating the number of atoms present in the group in a particular instance (e.g., "$C_{1-4}$alkyl," "$C_{3-6}$cycloalkyl," "$C_{1-4}$alkylene"). These designations are used as generally understood by those skilled in the art. For example, the representation "C" followed by a subscripted number indicates the number of carbon atoms present in the group that follows. Thus, "$C_3$alkyl" is an alkyl group with three carbon atoms (i.e., n-propyl, isopropyl). Where a range is given, as in "$C_{1-4}$," the members of the group that follows may have any number of carbon atoms falling within the recited range. A "$C_{1-4}$alkyl," for example, is an alkyl group having from 1 to 4 carbon atoms, however arranged (i.e., straight chain or branched).

In some embodiments, the method of inhibiting solid tumor metastasis includes administering an amount of a thromboxane A2 receptor antagonist effective to inhibit metastasis in combination with one or more chemotherapeutic agents. Chemotherapeutic agent refers to a chemical compound that is useful in the treatment of cancer. The compound may be a cytotoxic agent that affects rapidly dividing cells in general, or it may be a targeted therapeutic agent that affects the deregulated proteins of cancer cells. The chemotherapeutic agent may be an alkylating agent, an anti-metabolite, an anti-tumor antibiotic, an anti-cytoskeletal agent, a topoisomerase inhibitor, an anti-hormonal agent, a targeted therapeutic agent, an immunotherapy, or a combination thereof. Non-limiting examples of alkylating agents include altretamine, benzodopa, busulfan, carboplatin, carboquone, carmustine, chlorambucil, chlomaphazine, cholophosphamide, chlorozotocin, cisplatin, cyclosphosphamide, dacarbazine (DTIC), estramustine, fotemustine, ifosfamide, improsulfan, lomustine, mechlorethamine, mechlorethamine oxide hydrochloride, melphalan, meturedopa, nimustine, novembichin, phenesterine, piposulfan, prednimustine, ranimustine; temozolomide, thiotepa, triethylenemelamine, trietylenephosphoramide, triethylenethiophosphaoramide, trimethylolomelamine, trofosfamide, uracil mustard and uredopa. Suitable anti-metabolites include, but are not limited to aminopterin, ancitabine, azacitidine, 6-azauridine, capecitabine, carmofur, cytarabine or cytosine arabinoside (Ara-C), dideoxyuridine, denopterin, doxifluridine, enocitabine, floxuridine, fludarabine, 5-fluorouracil (5-FU), gemcetabine, leucovorin (folinic acid), 6-mercaptopurine, methotrexate, pemetrexed, pterop-terin, thiamiprine, trimetrexate, and thioguanine. Non-limiting examples of suitable anti-tumor antibiotics include aclacinomysin, actinomycin, adriamycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin. Non-limiting examples of suitable anti-cytoskeletal agents include colchicines, docetaxel, macromycin, paclitaxel (taxol), vinblastine, vincristine, vindesine, and vinorelbine. Suitable topoisomerase inhibitors include, but are not limited to, amsacrine, etoposide (VP-16), irinotecan, RFS 2000, teniposide, and topotecan. Non-limiting examples of suitable anti-hormonal agents such as aminoglutethimide, aromatase inhibiting 4(5) imidazoles, bicalutamide, finasteride, flutamide, goserelin, 4-hydroxytamoxifen, keoxifene, leuprolide, LY1 17018, mitotane, nilutamide, onapristone, raloxifene, tamoxifen, toremifene, and trilostane. No-limiting examples of targeted therapeutic agents include a monoclonal antibody such as alemtuzumab, bevacizumab, capecitabine, cetuximab, gemtuzumab, heregulin, rituximab, trastuzumab; a tyrosine kinase inhibitor such as imatinib mesylate; and a growth inhibitory polypeptide such as erythropoietin, interleukins (e.g., IL-1, IL-2, IL-3, IL-6), leukemia inhibitory factor, interferons, thrombopoietin, TNF-α, CD30 ligand, 4-1 BB ligand, and Apo-1 ligand. Also included are pharmaceutically acceptable salts, acids, or derivatives of any of the above listed agents. The mode of administration of the chemotherapeutic agent can and will vary depending upon the agent and the type of tumor or neoplasm. A skilled practitioner will be able to determine the appropriate dose of the chemotherapeutic agent.

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

Doses and Administration

Compositions used in the invention may be formulated as pharmaceutical compositions or formulations for oral, aerosol, parenteral, subcutaneous, intravenous, intramuscular, intraarterial, intrathecal, interperitoneal, nasal, rectal, topical, or vaginal administration. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

The pharmaceutical compositions and formulations may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their physiologically acceptable salts may be formulated for administration by, for example, solid dosing, eye drop, in a topical oil-based formulation, injection, inhalation (either through the mouth or the nose), implants, or oral, buccal, parenteral, or rectal administration. Techniques and formulations may generally be found in "Remington's Pharmaceutical Sciences," (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others.

Formulations suitable for oral administration can consist of (a) liquid solutions; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the therapeutic agent(s) in a flavor, usually sucrose and acacia or tragacanth, as well as pastilles comprising the therapeutic agent(s) in an inert base, such as gelatin and glycerin, or sucrose and acacia, emulsions, gels, and the like containing, in addition to, such excipients as are known in the art.

The therapeutic agent(s), alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The therapeutic agent can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,3-di-oxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include any bland fixed oil, e.g., petroleum, animal, vegetable, synthetic oils, or synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and mono glyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the therapeutic agent(s) in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Additionally, the therapeutic agent(s), or compositions comprising therapeutic agent, can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For purposes of all of the inventive methods, the administered amount or dose of the therapeutic agent(s) should be sufficient to effect a therapeutic response in the subject or animal over a reasonable time frame. For example, the dose of the therapeutic agent(s) should be sufficient to prevent or inhibit metastasis in a period of from about 2 hours or longer, e.g., 12 to 24 or more hours, from the time of administration. In certain embodiments, the time period could be even longer. The dose will be determined by the efficacy of the particular therapeutic or agent and the condition of the animal (e.g., human), as well as the body weight of the animal (e.g., human) to be treated. Many assays for determining an administered dose are known in the art. For purposes of the invention, an assay, which comprises comparing the extent to which the metastasis of a cancer cell is inhibited upon administration of a given dose of a therapeutic agent to a mammal among a set of mammals of which is each given a different dose of the therapeutic agent could be used to determine a starting dose to be administered to a mammal. The extent to which the metastasis of a cancer cell is inhibited or to which the tumor growth is inhibited upon administration of a certain dose can be assayed by methods known in the art.

The dose of the therapeutic agent also will be determined by the existence, nature and extent of any adverse side effects that might accompany the administration of a particular therapeutic agent. Typically, the attending physician will decide the dosage of the therapeutic agent with which to treat each individual patient, taking into consideration a variety of factors, such as age, body weight, general health, diet, sex, therapeutic agent to be administered, route of administration, and the severity of the condition being treated. By way of example and not intending to limit the present invention, the dose of the therapeutic agent can be about 0.001 to about 1000 mg/kg body weight of the subject being treated/day, from about 0.01 to about 10 mg/kg body weight/day, about 0.01 mg to about 1 mg/kg body weight/day, about 1 to about 100 mg/kg body weight/day, about 10 to about 90 mg/kg body weight/day, about 20 to about 80 mg/kg body weight/day, about 30 to about 70 mg/kg body weight/day, about 40 to about 60 mg/kg body weight/day, about 50 mg/kg body weight/day, about 100 to about 400 mg/kg body weight/day, about 200 to about 300 mg/kg body weight/day, or about 250 mg/kg body weight/day.

EXAMPLES

Association Between Thromboxane A2 Receptor Gain of Function and Metastasis

Figure 7:
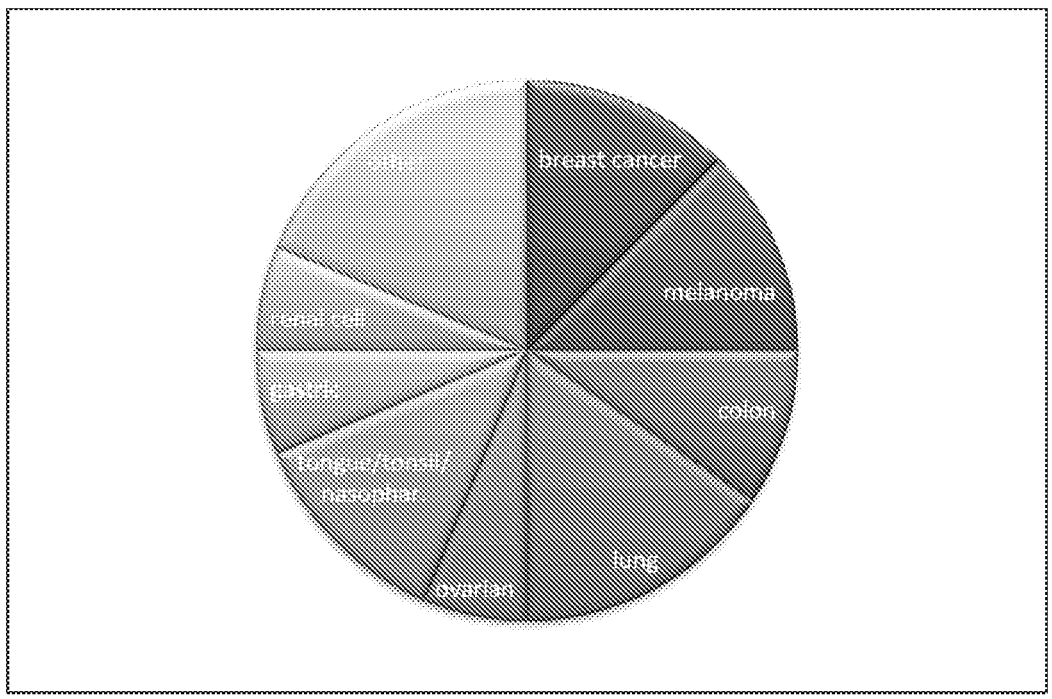
FIG. 7 shows primary tumor sites that resulted in the metastatic spread in patients having the gain of function variant T399A of the thromboxane A2 receptor.

Data from a Phenome Wide Association Study (PheWAS) show that a single nucleotide polymorphism (SNP) in the gene TBXA2R causes a gain-of-function variant (T399A) in the thromboxane A2 receptor strongly associating with increased tumor metastasis (N=32; P=0.003) (Table 1). FIG. 7 shows the primary tumor sites that resulted in the metastatic spread in patients having the gain of function variant T399A. In some embodiments, the invention provides a method of inhibiting solid tumor metastasis comprising administering to a subject with the T399A variant, an amount of a thromboxane A2 receptor antagonist effective to inhibit metastasis of a solid tumor in the subject.

TABLE 1

| Condition | Code | P-value | Odds Ratio | Case Carriers | Total Cases | Controls |
|---|---|---|---|---|---|---|
| Secondary malignant neoplasm | 198 | 3.8E−03 | 1.95 | 32 | 3568 | 20663 |
| Secondary malignancy of respiratory organs | 198.2 | 6.5E−03 | 2.42 | 13 | 1190 | 20663 |
| Secondary malignancy of lymph nodes | 198.1 | 7.0E−03 | 2.2 | 17 | 1698 | 20663 |
| Secondary malignant neoplasm of digestive systems | 198.3 | 1.2E−02 | 2.85 | 7 | 520 | 20663 |
| Secondary malignancy of brain/spine | 198.5 | 2.1E−02 | 2.68 | 7 | 587 | 20663 |

Figure 1:
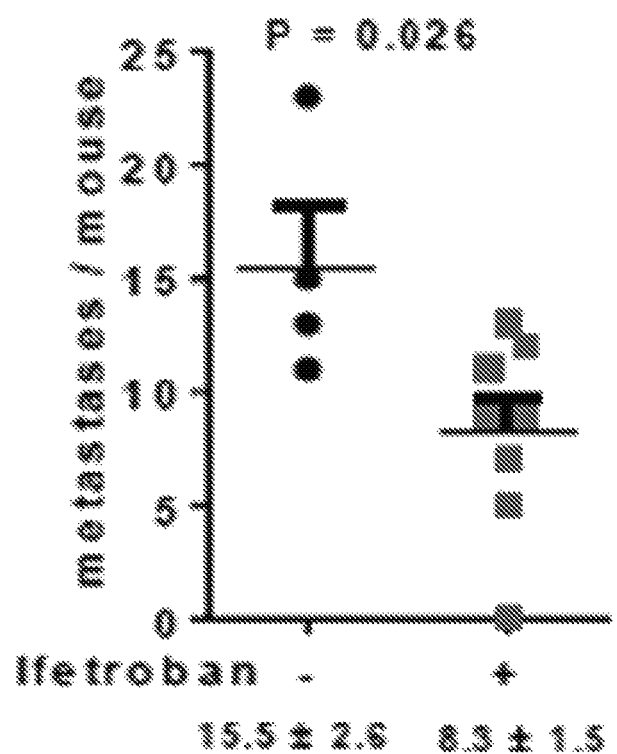
FIG. 1 shows the effects of ifetroban to decrease surface lung metastases from orthotopic primary 4T1 tumors in mice.
Figure 2:
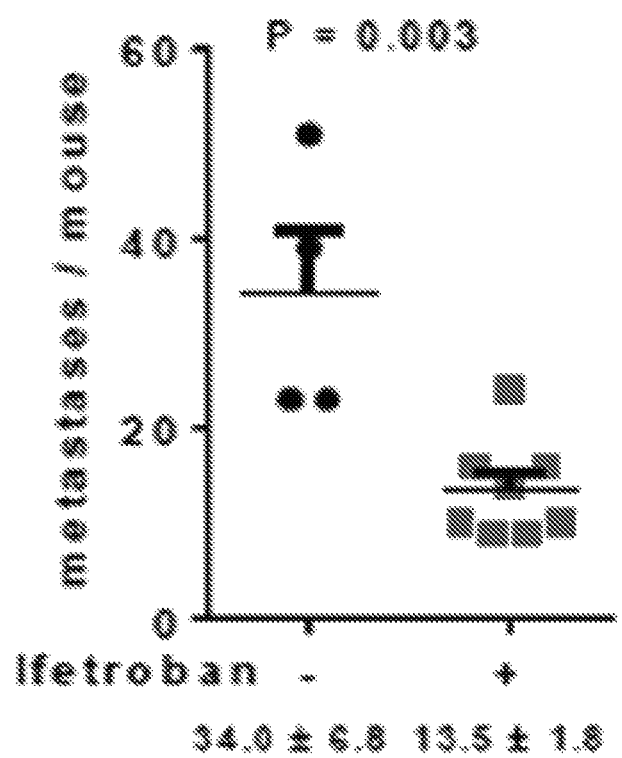
FIG. 2 shows the effects of ifetroban to decrease microscopic lung metastases from orthotopic primary 4T1 tumors in mice.

Ifetroban Decreases Both Macro- and Micrometastasis in the 4T1 Mouse Model of Metastasis $1 \times 10^5$ 4T1-RFP-luciferase cells were implanted into the left inguinal mammary fatpads of 6-week old, virgin WT Balb/C female mice using the following protocol. Mammary tumor cells (4T1-RFP-luciferase cells) are collected by trypsinization, counted, and resuspended in 50 microliters of serum-free media+50 microliters of growth factor-reduced Matrigel, for a total volume of 100 microliters. The cells are loaded into a syringe with a 26-g needle. The cells are injected into the inguinal mammary gland, which lies directly under (and attached to) the skin. The entire injection procedure takes about 10 seconds per mouse. Mice were treated by orogastric gavage with ifetroban (50 mg/kg daily) or vehicle control when average tumor volume reached 200 mm³, using 8 mice in the ifetroban treatment group, 4 mice in the control group, and 4% sucrose in water for the vehicle. Tumors, lungs and plasma were harvested approximately 3 weeks later. Lungs were assessed by whole mount hematoxylin staining to enumerate surface metastases (macro metastases) (FIG. 1). Lungs were sectioned and stained with hematoxylin and eosin to confirm that hematoxylin-stained nodules were metastatic lesions, and to enumerate microscopic metastases (FIG. 2).

Ifetroban Decreases Macrometastasis in the 4T1 Mouse Model of Metastasis (Second Experiment)

Figure 3:
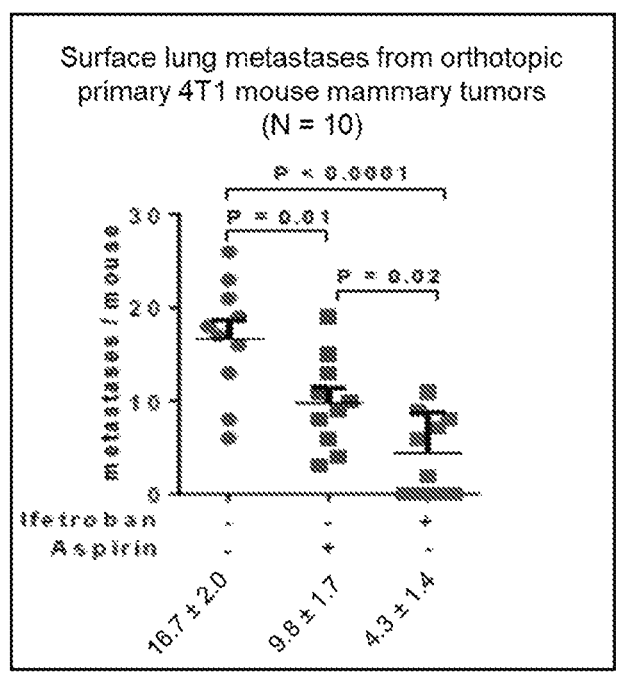
FIG. 3 shows the effects of ifetroban and aspirin to decrease metastasis in the 4T1 mouse model of metastasis.

$1 \times 10^5$ 4T1-RFP-luciferase cells were implanted into the left inguinal mammary fatpads of 6-week old, virgin WT Balb/C female mice as above. Mice were treated by orogastric gavage with ifetroban (50 mg/kg daily) or vehicle control when average tumor volume reached 50 mm³ as above. Additionally a third group was treated with aspirin (12 mg/kg daily). Lungs were harvested approximately 4 weeks later. Lungs were assessed by whole mount hematoxylin staining to enumerate surface metastases (macro metastases) (FIG. 3).

Ifetroban Decreases Metastases in MDA-MB-231 Mice.

Figure 4:
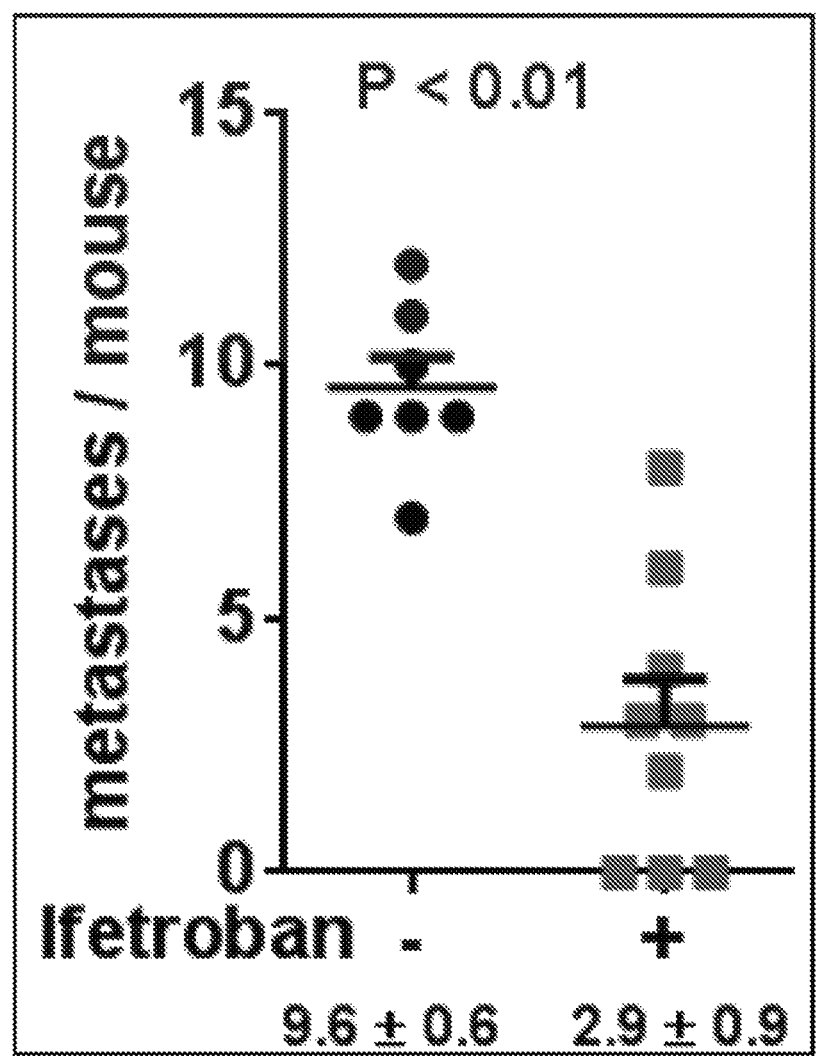
FIG. 4 shows the effects of ifetroban to decrease lung metastases in MDA-MB-231 mice.

Mice were randomized into groups receiving treatment by orogastric gavage with ifetroban (50 mg/kg daily) or vehicle, using 10 mice in both the ifetroban and control groups and 4% sucrose in water for the vehicle. Mice were treated 48 h prior to hematogenous delivery of MDA-MB-231 cells ($1 \times 10^5$ cells) by tail vein injection, and ifetroban treatment was continued for 3 weeks thereafter, at which point lungs were collected from each mouse, and lung metastatic lesions visible to the naked eye were counted (FIG. 4).

Figure 5A:
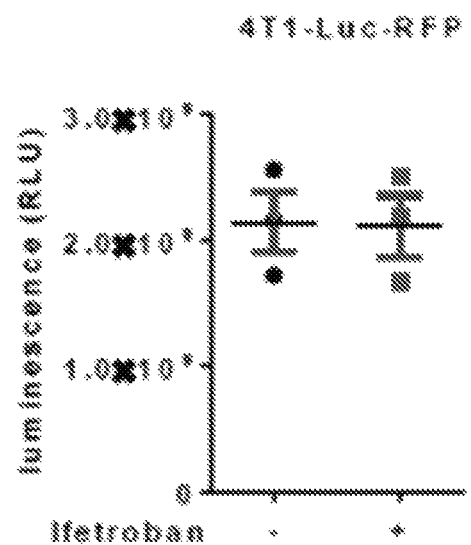
FIG. 5A shows that ifetroban has no effect on 4T1 cell growth and viability in vitro.

Ifetroban Treatment does not Affect Primary Tumor Volume, Mouse Bodyweight or the Survival of 4T1 Cells in Culture Cell culture experiments (in triplicate, repeated three times) performed using 4T1 cells treated for 96 hours with ifetroban, revealed no ifetroban-mediated changes in 4T1 cell number (automated cell counting), or in the number of apoptotic 4T1 cells (Annexin V staining) (FIG. 5A). For cell culture experiments, vehicle is PBS.

Figure 5B:
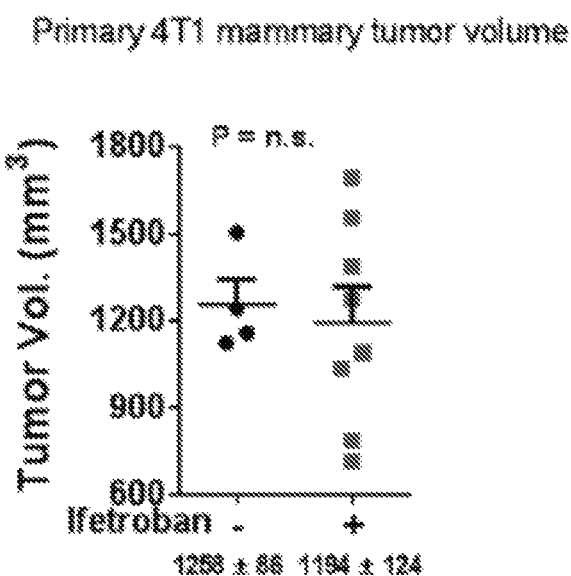
FIG. 5B shows that primary tumor volume in the 4T1 mouse model is not affected by ifetroban.
Figure 5C:
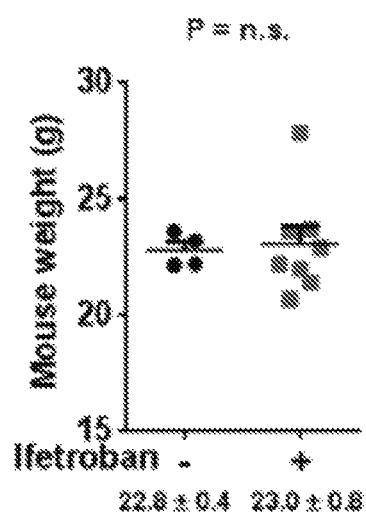
FIG. 5C shows that total mouse body weight is not affected by ifetroban.

$1 \times 10^5$ 4T1-RFP-luciferase cells were implanted into the left inguinal mammary fat pads of 6-week old, virgin WT Balb/C female mice. Mice were treated by orogastric gavage with ifetroban (50 mg/kg daily; N=8) or vehicle control (N=4) when average tumor volume reached 200 mm³. Ifetroban treatment (50 mg/kg daily) for 3 weeks did not affect primary tumor volume (FIG. 5B). Mouse total body weight was not affected by Ifetroban treatment (50 mg/kg daily) for 3 weeks (FIG. 5C).

Ifetroban Decreased Hematogenous Metastasis of Breast, Pancreatic and Lung Cancer Cells.

Figure 8:
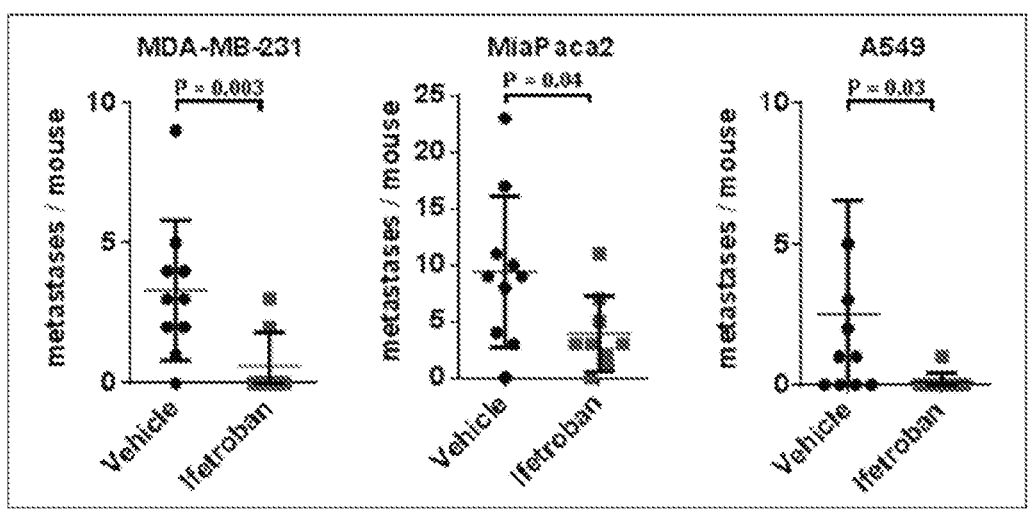
FIG. 8 shows decreased hematogenous metastasis of breast, pancreatic and lung cancer cells following administration of ifetroban.

MDA-MB-231 (breast), MiaPaca2 (pancreas) and A549 (lung) cancer cells were delivered by tail vein injection to nu/nu mice pre-treated 24 hours by orogastric gavage with ifetroban (50 mg/kg; N=10 per group) or vehicle (N=10). Mice continued daily treatment for an additional 21 days. On day 21, lungs were harvested and assessed for metastases. N=9, P value, Student's t-test. The results are shown in FIG. 8.

Ifetroban in Treating Patients with Malignant Solid Tumors at High Risk of Metastatic Recurrence (Prophetic Example).
Summary A pilot trial studies the side effects of ifetroban in treating patients with malignant solid tumors that are at high risk of coming back after treatment and spreading throughout the body. Platelets are a type of blood cells that help with clotting. Cancer cells stick to platelets and ride on them to get to different parts of the body. Drugs, such as ifetroban, may help these platelets become less "sticky," and reduce the chance of cancer cells spreading to other places in the body.

Detailed Study Description

PRIMARY OBJECTIVES: To assess the safety and feasibility of ifetroban sodium (ifetroban) administration in patients with malignant solid tumors at high risk of metastatic recurrence, after completion of all planned (neo) adjuvant locoregional and systemic therapies.

SECONDARY OBJECTIVES: To assess rate of metastatic recurrence after completion of ifetroban in patients with malignant solid tumors.

EXPLORATORY OBJECTIVES: To quantify pharmacodynamic markers of ifetroban effects.

OUTLINE: 60 patients are randomized to 1 of 2 groups. GROUP 1 (IFETROBAN): Patients receive 250 mg ifetroban sodium capsule orally (PO) once daily (QD). Courses repeat every 28 days for 12 months in the absence of disease progression or unacceptable toxicity. GROUP 2 (PLACEBO): Patients receive a 250 mg placebo capsule PO QD. Courses repeat every 28 days for 12 months in the absence of disease progression or unacceptable toxicity. After completion of study treatment, patients are followed up at 30 days, then up to 12 months.

Outcome Measures.

Primary Outcome Measures are: (1) Incidence of adverse events (Time Frame up to 30 days after completing treatment); (2) Adherence to treatment (participants will be provided a pill diary to record when they take their medication; study staff will collect the pill diary from participants at their clinic visits) (Time Frame up to 12 months); and (3) Summarized change of FACT-G score (scale=0 to 4) (Time Frame up to 12 months). Secondary Outcome Measures are (1) Percentage of patients within metastatic recurrence (within each cohort) (Time Frame at 12 months); and (2) Event-free survival (within each cohort) (Time Frame up to 12 months).

Eligibility Criteria

All adults aged 18 years or older.

Inclusion Criteria:

Signed and dated written informed consent.

Eastern Cooperative Oncology Group (ECOG) performance status 0, 1 or 2.

One of the following current diagnoses:
  Stage IIa to III triple negative breast cancer (TNBC).
  Stage I to II pancreatic adenocarcinoma.
  Lung Cancer: Stage IIa to III non-small cell lung cancer (NSCLC) or limited stage small cell lung cancer (SCLC).
  Stage IIa to III esophageal or gastroesophageal (GE) junction cancers (squamous cell carcinoma [SCCA] or adenocarcinoma).
  Stage IIa to III stomach cancer.

Patients must have completed all standard locoregional and systemic therapy for their cancer.

Administration of an investigational agent prior to enrollment needs to be completed at least 30 days prior to enrollment.

Patients must have recovered (≤grade 1 toxicities) from effects of local (surgery, radiation) or systemic treatments.

Platelet count ≥100,000 per mL of blood.

Hemoglobin ≥9/g/dL (may have been transfused).

Serum creatinine ≤1.5×upper limit of normal (ULN) or estimated creatinine clearance ≥50 mL/min as calculated using the Cockcroft-Gault (CG) equation.

Total serum bilirubin ≤1.5 times upper limit of normal (ULN).

Aspartate aminotransferase (AST/serum glutamic oxaloacetic transaminase [SGOT]) and alanine aminotransferase (ALT/serum glutamate-pyruvate transaminase [SGPT])≤2.5×ULN.

International normalized ratio (INR) below upper limit of normal (ULN).

Female patients of childbearing potential and non-sterile males must agree to use at least two methods of acceptable contraception from 15 days prior to first trial treatment administration until at least 5 months after study participant's final dose of study drug. Females of childbearing potential are defined as those who are not surgically sterile or post-menopausal (i.e. patient has not had a bilateral tubal ligation, a bilateral oophorectomy, or a complete hysterectomy; or has not been amenorrheic for 12 months without an alternative medical cause). Post-menopausal status in females under 55 years of age should be confirmed with a serum follicle-stimulating hormone (FSH) level within laboratory reference range for postmenopausal women. Non-sterile males are those who have not had a vasectomy with documentation of the absence of sperm in the ejaculate.

Patients unable to read/write in English are eligible to participate in the overall study but will not participate in the Patient-Reported Outcome questionnaires throughout the trial.

Re-enrollment of a subject that has discontinued the study as a pre-treatment screen failure (i.e. a consented patient who did not receive study drugs) is permitted. If reenrolled, the subject must be re-consented. Only the screening procedures performed outside of protocol-specified timing must be repeated.

Exclusion Criteria:

Clinical evidence of residual or distant disease after completion of standard treatment.

Current use of anti-platelet drugs (acetylsalicylic acid [ASA], nonsteroidal anti-inflammatory drugs [NSAIDs], clopidogrel, argatroban, etc.) or anticoagulants (warfarin, heparin products, etc.).

Active malignancy within 5 years prior to current diagnosis except for in situ disease or cancer with very high curability rate (i.e. testicular cancer, etc.).

Uncontrolled co-morbid serious systemic illnesses that in the opinion of the investigator could compromise therapeutic safety.

No concurrent anticancer therapy. Required washout from prior therapy:
  Chemotherapy: 21 days.
  Major surgery: 14 days (provided wound healing is adequate).
  Radiation: 7 days.
  Investigational/Biologic Therapy: 30 days.

Current symptomatic congestive heart failure (New York Heart Association >class II), unstable cardiac arrhythmia requiring therapy (e.g. medication or pacemaker), unstable angina (e.g. new, worsening or persistent chest discomfort), or uncontrolled hypertension (systolic >160 mmHg or diastolic >100 mmHg). Or any of the following occurring within 6 months (180 days) prior to first dose of study drugs: Myocardial infarction, coronary/peripheral artery bypass graft, cerebrovascular accident or transient ischemic attack. (Use of antihypertensive medication to control blood pressure is allowed.)

Ongoing peptic ulcer disease requiring treatment. History of gastrointestinal bleed. Severe gastro-esophageal reflux disease requiring treatment.

History of bleeding diathesis.

Planned elective major surgical intervention while taking ifetroban.

Pregnant or breastfeeding females.

Prisoners or subjects who are involuntarily incarcerated.

Known psychiatric condition, social circumstance, or other medical condition reasonably judged by the patient's study physician to unacceptably increase the risk of study participation; or to prohibit the understanding or rendering of informed consent or anticipated compliance with scheduled visits, treatment schedule, laboratory tests and other study requirements.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

For reasons of completeness, various aspects of the invention are set out in the following numbered clauses:

Clause 1. A method of inhibiting solid tumor metastasis comprising administering to a subject in need thereof, an amount of a thromboxane A2 receptor antagonist, or a pharmaceutically acceptable salt or composition thereof, effective to inhibit metastasis of a solid tumor in the subject.

Clause 2. The method of clause 1, wherein the amount of the thromboxane A2 receptor antagonist, or the pharmaceutically acceptable salt or composition thereof, is effective to inhibit the formation of circulating tumor cell clusters.

Clause 3. The method of clause 1 or 2, wherein the amount of the thromboxane A2 receptor antagonist, or the pharmaceutically acceptable salt or composition thereof, is effective to inhibit movement of circulating tumor cell clusters.

Clause 4. The method of any of clauses 1-3, wherein the amount of the thromboxane A2 receptor antagonist, or the pharmaceutically acceptable salt or composition thereof, is effective to inhibit the aggregation of circulating tumor cell clusters with platelets.

Clause 5. The method of any of clauses 1-4, wherein the amount of the thromboxane A2 receptor antagonist, or the pharmaceutically acceptable salt or composition thereof, is effective to inhibit integrin- and/or selectin-mediated cell survival signaling.

Clause 6. The method of any of clauses 1-5, wherein the amount of the thromboxane A2 receptor antagonist, or the pharmaceutically acceptable salt or composition thereof, is effective to reduce the rate of metastatic recurrence.

Clause 7. The method of any of clauses 1-6, wherein the thromboxane receptor antagonist is ifetroban, GR32191, SQ29548, sulotroban, daltroban, linotroban, ramatroban, seratrodast, terutroban, Z-235, LCB-2853, SQ28668, ICI 192605, AH23848, ONO3708, CPI-211, or pinane $TXA_2$.

Clause 8. The method of clause 7, wherein the thromboxane receptor antagonist is ifetroban.

Clause 9. The method of any of clauses 1-6, wherein the thromboxane receptor antagonist is a compound of formula (I),

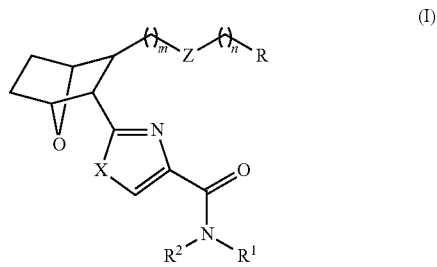

(I)

including all stereoisomers thereof, wherein
m is 1, 2, or 3;
n is 0, 1, 2, 3, or 4;
Z is —$(CH_2)_2$—, —CH=CH—, or

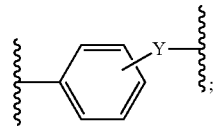

Y is O, a single bond, or —CH=CH—;
R is $CO_2H$, —$CO_2C_{1-6}$alkyl, $CH_2OH$, —$CONHSO_2R^3$, —$CONHR^{3a}$, or —$CH_2$-tetrazol-5-yl;
$R^3$ is $C_{1-6}$alkyl, 6- to 10-membered aryl, or -$L^1$-(6- to 10-membered aryl);
$R^{3a}$ is $C_{1-6}$alkyl, 6- to 10-membered aryl, or -$L^1$-(6- to 10-membered aryl);
X is O, S, or NH;
$R^1$ is hydrogen, $C_{1-8}$alkyl, $C_{2-8}$alkenyl, $C_{2-8}$alkynyl, $G^1$, -$L^1$-$G^1$, —$(CH_2)_t$—C(O)—$NHR^{1a}$, or —$(CH_2)_t$—NH—C(O)$R^{1a}$;
$G^1$ is a 6- to 10-membered aryl, a $C_{3-12}$cycloalkyl, a 5- to 12-membered heteroaryl, or a 4- to 12-membered heterocyclyl;
$L^1$ is $C_{1-6}$alkylene;
t is 1 to 12;
$R^{1a}$ is $C_{1-6}$alkyl, $C_{3-12}$cycloalkyl, -$L^1$-$C_{3-12}$cycloalkyl, or a 6- to 10-membered aryl;
$R^2$ is hydrogen, $C_{1-6}$alkyl, 6- to 10-membered aryl, or -$L^1$-(6- to 10-membered aryl);
or $R^1$ and $R^2$ together with the nitrogen to which they attach form a 4- to 8-membered heterocyclic ring;

wherein each aryl is independently and optionally substituted with 1 or 2 substituents independently selected from the group consisting of halogen, cyano, $C_{1-6}$alkyl, $C_{1-6}$haloalkyl, OH, —$OC_{1-6}$alkyl, —$OC_{1-6}$haloalkyl, —$SC_{1-6}$alkyl, —$S(O)C_{1-6}$alkyl, —$S(O)_2C_{1-6}$alkyl, —$OC_{1-6}$alkylene-phenyl, —S-phenyl, —S(O)-phenyl, and —$S(O)_2$-phenyl;

wherein each cycloalkyl is independently and optionally substituted with 1-4 substituents independently selected from the group consisting of halogen, $C_{1-6}$alkyl, $C_{1-6}$haloalkyl, OH, and —$OC_{1-6}$alkyl.

Clause 10. The method of clause 9, wherein the compound of formula (I) has formula (I-h)

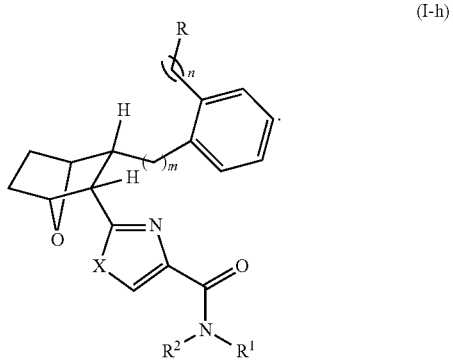

(I-h)

Clause 11. The method of clause 9 or 10, wherein R is $CO_2H$, or an alkali metal salt thereof.

Clause 12. The method of any of clauses 9-11, wherein m is 1, n is 2, $R^2$ is hydrogen, and $R^1$ is $C_{1-8}$alkyl.

Clause 13. The method of any of clauses 9-12, wherein X is O.

Clause 14. The method of any of clauses 1-13, wherein the subject has a primary tumor of a cancer selected from the group consisting of lung cancer, non-small cell lung cancer, breast cancer, ovarian cancer, prostate cancer, testicular cancer, pancreatic cancer, melanoma, sarcoma, cervical cancer, endometrial cancer, liver cancer, uterine cancer, kidney cancer, gastroesophageal cancer, colon cancer, bladder cancer, mouth cancer, and throat cancer.

Clause 15. The method of any of clauses 1-14, wherein the amount of the thromboxane A2 receptor antagonist, or the pharmaceutically acceptable salt or composition thereof, is effective to inhibit metastasis of the solid tumor in the subject without inhibiting the growth or development of the solid tumor.

Clause 16. The method of any of clauses 1-15, further comprising administering at least one chemotherapeutic agent chosen from an alkylating agent, an anti-metabolite, an anti-tumor antibiotic, an anti-cytoskeletal agent, a topoisomerase inhibitor, an antihormonal agent, a targeted therapeutic agent, immunotherapy, and combinations thereof.

Clause 17. The method of any of clauses 1-16, wherein the thromboxane A2 receptor antagonist, or the pharmaceutically acceptable salt or composition thereof, is administered after a chemotherapy treatment regimen.

Clause 18. The method of any of the foregoing clauses, wherein the subject has a T399A gain of function mutation of the thromboxane A2 receptor.

Clause 19. A thromboxane A2 receptor antagonist, or a pharmaceutically acceptable salt or composition thereof, for use in the treatment or inhibition of solid tumor metastasis in a subject.

Clause 20. A thromboxane A2 receptor antagonist, or a pharmaceutically acceptable salt or composition thereof, for use in a method of treating or inhibiting solid tumor metastasis, wherein the method comprises administering the thromboxane A2 receptor antagonist to a subject in need thereof.

Clause 21. Use of a thromboxane A2 receptor antagonist, or a pharmaceutically acceptable salt or composition thereof, for the preparation of a medicament for the treatment or inhibition of solid tumor metastasis in a subject.

We claim:

1. A method of inhibiting solid tumor metastasis comprising administering to a subject in need thereof, an amount of a thromboxane A2 receptor antagonist, or a pharmaceutically acceptable salt or composition thereof, effective to reduce the rate of metastatic recurrence in the subject,
wherein the thromboxane receptor antagonist is a compound of formula (I-h)

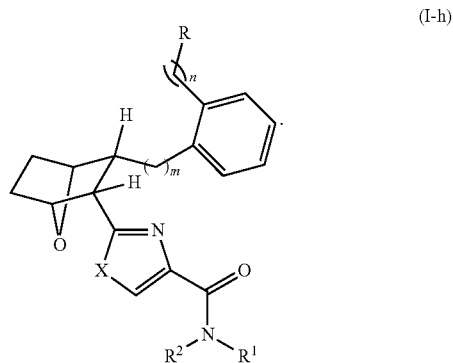

(I-h)

wherein:
m is 1, 2, or 3;
n is 0, 1, 2, 3, or 4;
R is $CO_2H$, —$CO_2C_{1-6}$alkyl, $CH_2OH$, —$CONHSO_2R^3$, —$CONHR^{3a}$, or —$CH_2$-tetrazol-5-yl;
X is O, S, or NH;
$R^1$ is hydrogen, $C_{1-8}$alkyl, $C_{2-8}$alkenyl, $C_{2-8}$alkynyl, $G^1$, -$L^1$-$G^1$, —$(CH_2)_t$—C(O)—$NHR^{1a}$, or —$(CH_2)_t$—NH—$C(O)R^{1a}$;
$G^1$ is a 6- to 10-membered aryl, a $C_{3-12}$cycloalkyl, a 5- to 12-membered heteroaryl, or a 4- to 12-membered heterocyclyl;
$L^1$ is $C_{1-6}$alkylene;
t is 1 to 12;
$R^{1a}$ is $C_{1-6}$alkyl, $C_{3-12}$cycloalkyl, -$L^1$-$C_{3-12}$cycloalkyl, or a 6- to 10-membered aryl;
$R^2$ is hydrogen, $C_{1-6}$alkyl, 6- to 10-membered aryl, or -$L^1$-(6- to 10-membered aryl);
or $R^1$ and $R^2$ together with the nitrogen to which they attach form a 4- to 8-membered heterocyclic ring;
wherein each aryl is independently and optionally substituted with 1 or 2 substituents independently selected from the group consisting of halogen, cyano, $C_{1-6}$alkyl, $C_{1-6}$haloalkyl, OH, —$OC_{1-6}$alkyl, —$OC_{1-6}$haloalkyl, —$SC_{1-6}$alkyl, —$S(O)C_{1-6}$alkyl, —$S(O)_2C_{1-6}$alkyl, —$OC_{1-6}$alkylene-phenyl, —S-phenyl, —S(O)-phenyl, and —$S(O)_2$-phenyl;
wherein each cycloalkyl is independently and optionally substituted with 1-4 substituents independently selected from the group consisting of halogen, $C_{1-6}$alkyl, $C_{1-6}$haloalkyl, OH, and —$OC_{1-6}$alkyl.

2. The method of claim 1, wherein the thromboxane receptor antagonist is ifetroban.

3. The method of claim 2, wherein the amount of the ifetroban, or the pharmaceutically acceptable salt or composition thereof, is effective to inhibit movement of circulating tumor cell clusters.

4. The method of claim 2, wherein the amount of the ifetroban, or the pharmaceutically acceptable salt or composition thereof, is effective to inhibit the aggregation of circulating tumor cell clusters with platelets.

5. The method of claim 2, wherein the amount of the ifetroban, or the pharmaceutically acceptable salt or composition thereof, is effective to inhibit integrin- and/or selectin-mediated cell survival signaling.

6. The method of claim 2, wherein the amount of the ifetroban, or the pharmaceutically acceptable salt or composition thereof, is effective to inhibit the formation of circulating tumor cell clusters.

7. The method of claim 1, wherein R is $CO_2H$, or an alkali metal salt thereof.

8. The method of claim 7, wherein m is 1, n is 2, $R^2$ is hydrogen, and $R^1$ is $C_{1-8}$alkyl.

9. The method of claim 8, wherein X is O.

10. The method of claim 2, wherein the subject has a primary tumor of a cancer selected from the group consisting of lung cancer, non-small cell lung cancer, breast cancer, ovarian cancer, prostate cancer, testicular cancer, pancreatic cancer, melanoma, sarcoma, cervical cancer, endometrial cancer, liver cancer, uterine cancer, kidney cancer, gastroesophageal cancer, colon cancer, bladder cancer, mouth cancer, and throat cancer.

11. The method of claim 2, wherein the amount of the ifetroban, or the pharmaceutically acceptable salt or composition thereof, is effective to inhibit metastasis of the solid tumor in the subject without inhibiting the growth or development of the solid tumor.

12. The method of claim 2, further comprising administering at least one chemotherapeutic agent chosen from an alkylating agent, an anti-metabolite, an anti-tumor antibiotic, an anti-cytoskeletal agent, a topoisomerase inhibitor, an antihormonal agent, a targeted therapeutic agent, immunotherapy, and combinations thereof.

13. The method of claim 2, wherein the ifetroban, or the pharmaceutically acceptable salt or composition thereof, is administered after a chemotherapy treatment regimen.

14. The method of claim 2, wherein the subject has a T399A gain of function mutation of the thromboxane A2 receptor.

* * * * *